United States Patent [19]
Tang et al.

[11] Patent Number: 5,674,275
[45] Date of Patent: Oct. 7, 1997

[54] POLYACRYLATE AND POLYMETHACRYLATE ESTER BASED HYDROGEL ADHESIVES

[75] Inventors: Jinsong Tang; Norbert J. Mruk, both of Williamsville, N.Y.

[73] Assignee: Graphic Controls Corporation, Buffalo, N.Y.

[21] Appl. No.: 478,495

[22] Filed: Jun. 7, 1995

Related U.S. Application Data

[60] Continuation-in-part of Ser. No. 408,625, Mar. 22, 1995, Pat. No. 5,614,586, which is a division of Ser. No. 223,550, Apr. 6, 1994, abandoned.

[51] Int. Cl.$^6$ ............................................. A61N 1/04
[52] U.S. Cl. ..................... 607/152; 128/639; 604/307; 427/2.12
[58] Field of Search .................... 607/153, 152; 128/639, 640, 641, 642; 624/304, 305, 306, 307, 20

[56] References Cited

U.S. PATENT DOCUMENTS

| | | |
|---|---|---|
| 3,024,221 | 3/1962 | LeFevre . |
| 3,033,833 | 5/1962 | LeFevre . |
| 4,524,087 | 6/1985 | Engel ............................ 128/640 |
| 4,699,146 | 10/1987 | Sieverding ..................... 128/640 |
| 4,737,410 | 4/1988 | Kantner ........................ 428/343 |
| 4,814,215 | 3/1989 | Lautenschlaeger et al. . |
| 4,842,768 | 6/1989 | Nakao et al. . |
| 4,848,353 | 7/1989 | Engel . |
| 4,860,754 | 8/1989 | Sharik et al. . |
| 4,871,812 | 10/1989 | Lucast et al. . |
| 4,931,347 | 6/1990 | Slovinsky et al. . |
| 4,947,847 | 8/1990 | Nakao et al. . |
| 5,124,076 | 6/1992 | Smuckler . |
| 5,135,755 | 8/1992 | Czech et al. ................. 424/445 |
| 5,141,789 | 8/1992 | Matsuzawa et al. ............ 428/40 |
| 5,143,071 | 9/1992 | Keusch et al. ................ 128/640 |
| 5,183,599 | 2/1993 | Smuckler . |
| 5,336,501 | 8/1994 | Czech et al. ................. 424/445 |

FOREIGN PATENT DOCUMENTS

| | | |
|---|---|---|
| 0352442A2 | 1/1990 | European Pat. Off. . |
| 0352442A3 | 1/1990 | European Pat. Off. . |
| 0382128A2 | 8/1990 | European Pat. Off. . |
| 0382128A3 | 8/1990 | European Pat. Off. . |
| WO8805060 | 7/1988 | WIPO . |

OTHER PUBLICATIONS

S. Pikorny and J. Dnebosky, "The Effect of Acrylic Acid Dimer on the Properties of Carboxycement", J. Dent. 1988; 16: 76–79.
Search Report.

*Primary Examiner*—Christopher Henderson
*Attorney, Agent, or Firm*—Ratner & Prestia

[57] ABSTRACT

A hydrogel adhesive made of a polymer formed by polymerizing a water soluble long chain (meth)acrylate ester monomer (structure I); a hydrogel adhesive made of a copolymer formed by copolymerizing a first water soluble long chain (meth)acrylate ester monomer (structure I) with a second water soluble monomer (structure II); biomedical devices having such hydrogel adhesives; a method of preparing hydrogel adhesives; and a method of adhering biomedical devices to skin.

8 Claims, 4 Drawing Sheets

POLYACRYLATE AND POLYMETHACRYLATE ESTER BASED HYDROGEL ADHESIVES

This application is a continuation-in-part of U.S. patent application Ser. No. 08/408,625, filed Mar. 22, 1995, now U.S. Pat. No. 5,614,586, which, in turn, is a divisional of U.S. patent application Ser. No. 08/223,550, filed Apr. 6, 1994 now abandoned.

FIELD OF THE INVENTION

This invention relates to hydrogel adhesives and, more particularly, to polyacrylate and polymethacrylate ester based hydrogel adhesives used with biomedical devices.

BACKGROUND OF THE INVENTION

In the medical field, when a biomedical electrode is used on a patient, it is generally provided with a metallic plate attached to conductive wires which are, in turn, attached to a monitoring apparatus. To improve conductivity between the skin and the electrode, a composition, usually a paste, a gel, or a cream, is applied between the metallic plate and the skin. The use of such a composition is often messy and offensive to the patient. In addition, the composition must be removed from the skin after use, either by wiping or by the use of solvents, both of which are also offensive. Furthermore, the electrode is usually secured to the patient by tape having a conventional pressure sensitive adhesive (PSA) thereon. Removal of the tape causes discomfort to the patient, and the composition of the adhesive of the tape may induce an allergic reaction in the patient.

To circumvent these difficulties, electrically conductive hydrogel adhesives have been developed. These hydrogel adhesives have replaced pastes, gels, and creams because they advantageously provide both conductivity and clean, residue-free removal from the skin surface after use. In addition, depending on the particular application and electrode design and on the nature of the hydrogel adhesive, hydrogel adhesives can be used alone-without a conventional PSA to secure the electrode to the skin. This is a result of the hydrogel's own specific adhesive properties.

Hydrogel adhesives differ from conventional PSA's in several respects. PSA's generally consist of polyacrylate polymer, or a polyolefin polymer combined with a tackifier additive. Monomers used to prepare polyacrylate PSA's are long chain esters of acrylic acid such as octyl acrylate. These particular polymers are inherently tacky and adhesive in nature. Polyolefin-based PSA's are prepared from rubber-like polymers such as polybutylene. Because these polymers are not inherently tacky, a tackifier is blended into the polymer base. Terpenes are generally used as tackifiers in these compositions. Most significantly, a conventional PSA contains no solvent, is non-aqueous, and will not dry out. These polymers are inherently adhesive and do not depend upon a swollen, crosslinked, watery formulation to provide tackiness and peel adhesion. They cannot be made electrically conductive by addition of water and electrolyte and they tend to be less skin friendly than hydrogel adhesives. Examples of typical PSA's are the adhesives coated on "Scotch" brand cellophane tape, masking tape, medical adhesive tape, and "Band-Aid" brand adhesive bandages.

Hydrogel skin adhesives have proven useful in a variety of applications involving biomedical electrodes. Examples of such applications include use with electrocardiographic (ECG) electrodes, electrosurgical grounding pads, defibrillation electrodes, transcutaneous nerve stimulation electrodes, and iontophoretic drug delivery electrodes. Non-electrode applications are also becoming increasingly important. Examples include use with transdermal drug delivery patches, as adhesives for ostomy devices, as wound dressings, and with medical tapes.

Hydrogel skin adhesive compositions are generally composed of a crosslinked water soluble polymer network swollen with water as a solvent component. Humectant materials are usually added as co-solvents to provide slow drying or non-drying characteristics to the hydrogel adhesive. Humectant materials are usually polyols such as glycerol, sorbitol, or propylene glycol, or low molecular weight polyethylene oxide diols such as PEG 400 or PEG 600. Other additives can also be added to hydrogel adhesives for specific purposes. Examples include electrolytes such as sodium chloride for electrical conductivity, preservatives such as methyl paraben to prevent microbiological degradation, buffering agents such as sodium dihydrogen phosphate for pH control, and water soluble polymers such as polyacrylamide for viscosity modification.

The crosslinked water soluble polymer network can be formed by polymerization of a large variety of water soluble monomers in the presence of difunctional crosslinking agents by free radical polymerization techniques initiated by thermal or photochemical methods. Crosslinking of previously formed water soluble polymers can also be effected by complexation with difunctional species, such as divalent metal cations or difunctional organic reactants, or by exposure to ionizing radiation such as gamma-rays or electron beams. Many naturally occurring polymers such as gelatin can be reversibly and non-covalently crosslinked by manipulating gelation temperatures.

Examples of water soluble monomers subject to free radical polymerization for use as a hydrogel are acrylic acid, methacrylic acid, acrylamide, methacrylamide, and vinyl pyrrolidone. Diacrylate esters of polyethylene oxides are typical free radical crosslinking agents used in these compositions. Examples of hydrogel formation by the crosslinking of water soluble polymers are the crosslinking of carboxymethylcellulose by reaction with aluminum ion, the crosslinking of prepolymer polyisocyanates by reaction with water and organic diols, and the crosslinking of polyvinylpyrrolidone by electron beam radiation. Examples of naturally occurring polymers which form gels by thermal gelation are gelatin and karaya gum. There are thus a large number of hydrogel adhesives of diverse types.

One of the critical properties determining the usefulness of a hydrogel adhesive is its peel adhesion strength. High peel strength allows the hydrogel adhesive to be used without an accompanying PSA in many applications. Hydrogel skin adhesives with high peel strength provide a more secure attachment of electrodes (or other devices) to the patient. Correspondingly, low peel strength provides a less secure attachment, allowing easier removal of the hydrogel adhesive from the patient. Depending on the particular application, varying hydrogel adhesive peel strengths are required.

Another useful property of hydrogel adhesives is repositionability. "Repositionability" is defined as the ability of the adhesive hydrogel to be removed from one area of the skin and to be attached to another area without loss of peel adhesion properties. Other properties of hydrogel adhesives include tack adhesion and creep compliance.

The properties of a given hydrogel adhesive depend in large measure upon the nature of the crosslinked water soluble polymer that comprises the hydrogel adhesive.

Presently, the nature of the crosslinked water soluble polymer used in the hydrogel adhesive fixes the properties of that adhesive. In order to vary the peel strength or repositionability of the adhesive, for example, different water soluble polymers may be used. Development of hydrogel adhesive properties is thus an empirical process at present. A water soluble polymer system that allows broad variation of hydrogel adhesive properties without changing the type of polymer is desirable.

Other desirable characteristics of skin adhesives include: skin-friendliness, conductivity, and permeability. Skin-friendliness means nonirritating, nonsensitizing, and noncytotoxic, requiring no precleaning and leaving no residue, with nontraumatic removal of the adhesive from the skin. Good conductivity is essential for many of the applications listed above, such as transcutaneous electrical nerve stimulation electrodes, electrosurgical grounding pads, electrocardiographic electrodes, and defibrillation electrodes. Permeability refers to the ability of the adhesive, in conjunction with the substrate upon which the adhesive is disposed, to pass moisture absorbed from a patient's skin through the adhesive and the substrate and out of the system to the surrounding atmosphere. This prevents weakening of the bonding strength of the adhesive and injury to the skin.

SUMMARY OF THE INVENTION

The present invention provides a hydrogel adhesive made of a polymer formed by polymerizing a monomer having the structure (I)

$$CH_2=C(R_1)-C(O)-O-R_2-X \quad (I)$$

where $R_1$ is selected from H and $CH_3$; $R_2$ is selected from a straight or branched chain alkyl radical of 2–12 carbon atoms, a straight or branched chain aliphatic ester radical of 5–12 carbon and oxygen atoms, and a straight or branched chain ether radical of 3–12 carbon and oxygen atoms; X is an ionic group selected from $SO_3^-$, $COO^-$, and $$-{}^+N(R_3)(R_4)(R_5)$$

where $R_3$, $R_4$, and $R_5$ are independently selected from H and alkyl groups of 1–4 carbon atoms.

Also provided is a method of adhering a biomedical device to skin by disposing between the device and the skin the above hydrogel adhesive and applying sufficient pressure to the device to adhere it to the skin. A biomedical device with a surface adapted to be adhered to the skin of a patient, wherein the surface has the above hydrogel adhesive disposed thereon, is also provided by the present invention.

Also provided is a method of preparing the above hydrogel adhesive by polymerizing monomer (I) in the presence of multifunctional crosslinking agents by free radical polymerization techniques using an initiator.

The invention further provides a compound that is a copolymer formed by copolymerizing a first water soluble monomer having the structure (I) with a second water soluble monomer having the structure (II)

$$CH_2=CH-Y \quad (II)$$

where Y is selected from

—COOH;

$$-C(O)-N(R_6)(R_7); \quad -N\underset{}{\overset{}{\bigcirc}};$$

—$SO_3H$; and —$PO_3H$ where $R_6$ and $R_7$ are independently selected from H and alkyl groups of 1–3 carbon atoms.

Also provided is a hydrogel adhesive comprising a copolymer formed by copolymerizing the first and second water soluble monomers (I) and (II) above.

Also provided is a method of adhering a biomedical device to skin by disposing between the device and the skin a hydrogel adhesive made from monomers (I) and (II), as described above, and applying sufficient pressure to the device to adhere it to the skin.

Also provided is a biomedical device with a surface adapted to be adhered to the skin of a patient, wherein the surface has a hydrogel adhesive made from monomers (I) and (II) as described above. The device may include a gas permeable substrate adjacent to the hydrogel adhesive.

Also provided is a method of preparing a hydrogel adhesive by copolymerizing monomers (I) and (II) in the presence of multifunctional crosslinking agents by free radical polymerization techniques using an initiator.

BRIEF DESCRIPTION OF THE DRAWING

The invention is best understood from the following detailed description when read in connection with the accompanying drawing, in which.

DETAILED DESCRIPTION OF THE INVENTION

The present invention involves hydrogel adhesives having variable properties depending on the relative proportions of the first and second water soluble monomers used in the formulation of the adhesive. The general formula for the first monomer is given above as formula I.

Two specific monomers within the scope of general formula I are potassium-3-sulfopropyl acrylate (SPAK) and 2-carboxyethylacrylate (CEA). CEA is particularly preferred when it is in the form of a partially neutralized alkali metal salt. The structures for these water soluble monomers are:

A. SPAK

B. CEA

The two formula I monomers given above are acrylate ester monomers. Other monomers having the general structure of formula I are methacrylate ester monomers such as 2-sulfoethylmethacrylate (SEMA), potassium-3-sulfopropyl methacrylate (SPMAK), and methacryloxyethyl trimethylammonium chloride (MAETAC).

The general formula for the second monomer used in the hydrogel adhesive compositions of the present invention is given above as formula II. The second monomer has a pendant chain smaller in molecular size than that of the first monomer. Examples of monomers of formula II are acrylic acid, acrylamide, alkylated acrylamides, vinyl pyrrolidone, vinyl sulfonic acid, and vinyl phosphonic acid.

A hydrogel adhesive formed by polymerizing a formula I monomer without a formula II monomer (a homopolymer of the formula I monomer) will possess certain adhesive properties. By adding increasing amounts of the formula II monomer and polymerizing to form a copolymer of formula I and II monomers, the adhesive properties vary, depending on the relative proportions of the formula I and II monomers.

The preparation and composition of an adhesive hydrogel using a homopolymer of SPAK (100% of first water soluble polymer—SPAK; 0% of second water soluble polymer) is first described below. This serves as a general description of the procedure used to formulate the adhesive poly(meth)acrylate ester hydrogels of the invention. (The final composition of the hydrogel formed of the homopolymer of SPAK is given as Example 1 in Table 1; the compositions of all other examples disclosed herein are presented in the accompanying Tables 1–6 as Examples 2–34.)

A mixture of potassium chloride (0.5 g) and potassium-3-sulfopropylacrylate (35.0 g) was dissolved in 40.5 g of distilled water with stirring. Polyacrylamide N-300 LMW (2.0 g) (available from American Cyanamid Co. of Wayne, N.J. 07470) was then added and dispersed into the above solution with vigorous stirring. The polyacrylamide dissolved slowly over a period of a few hours with a corresponding increase in the viscosity of the solution. Glycerin (20.0 g); a 3% solution of N,N'methylenebis acrylamide in propylene glycol (1.2 g); and Darocur 1173 (0.8 g) (available from EM Industries Inc. of Hawthorne, N.Y. 10532) were then added sequentially, with stirring, resulting in a moderately viscous, homogeneous solution.

The finished composition was coated onto a polycarbonate film having a thickness of 2.5 mil, using a 30 mil wet-film applicator. The coating was cured with a Fusion 200 W/in. UV lamp (H-bulb) at a bulb height of approximately 12 inches with a UV dosage of 0.69 J/cm². A hydrogel adhesive was thus formed of a homopolymer of SPAK.

To measure peel adhesion, the coated hydrogel adhesive films were attached to a ⅛ inch thick polyethylene foam substrate and pulled off at a 90 angle at a rate of 6 inches per minute. The results are reported as grams per ⅞ inch width of sample. Other properties measured were tack adhesion, creep compliance, and repositionability. Tack adhesion was measured using a Polyken Tack instrument (2 sec. dwell, 1 cm/sec. speed, 20 grams force). Repositionability was measured by repeatedly pulling the adhesive off the foam substrate and measuring changes in peel adhesion.

In the description given above for the formation of an adhesive hydrogel, the distilled water serves as a solvent and potassium chloride is added as an electrolyte to provide electrical conductivity to the compositions of the invention when they are used as biomedical electrode adhesives. Potassium hydroxide is used to partially neutralize acrylate monomers containing carboxylic acid groups such as acrylic acid. Polyacrylamide polymer (PAAm N-300 LMW) serves as a viscosity modifier. Glycerin serves as a humectant. Used as a cross-linking monomer for the hydrogel homopolymer is N,N'-methylenebis acrylamide (MBA) which, as described above, is added as a 3% solution in propylene glycol. (Although a difunctional cross-linking agent is used in this example, other multifunctional agents can be used. Thus, in this application, the term "multifunctional" includes difunctional, trifunctional, tetrafunctional, etc.) Darocur 1173 (2-hydroxy-2-methyl-1-phenyl-propane-1-one) serves as the photoinitiator in the UV polymerization reaction.

The homopolymer of SPAK in the form of an adhesive hydrogel, synthesized as described in Example 1, exhibits a low peel strength (thereby minimizing risk of injury and discomfort to the patient) of 40 g as shown in Table 1, Example 1. The homopolymer also has good repositionability when attached to the skin. In terms of repositionability, the homopolymer of SPAK is superior to other hydrogel homopolymers such as polyacrylic acid.

Repositionability and low peel strength properties of hydrogel skin adhesives such as that formed of the SPAK homopolymer are important in biomedical applications such as diagnostic ECG electrodes, wound dressings, and medical tapes used to secure devices such as intravenous catheters to the body. Medical applications in the pediatric, neonatal, geriatric, and operating room areas are particularly relevant because of the high degree of skin sensitivity typically exhibited by patients within these hospital groupings.

To vary the properties of the hydrogel adhesive and provide greater peel strength, increased amounts (from 0% in the preceding example) of the second water soluble monomer are added and polymerized with the first monomer.

The preparation and composition of an adhesive hydrogel using a copolymer of SPAK and acrylic acid (AA) is next described. This serves as a description of the procedure used to formulate the adhesive copolymer poly(meth)acrylate ester hydrogels of the invention. The final composition of the hydrogel formed of the copolymer of this example is given as Example 4 in Table 1.

A mixture of potassium chloride (0.5 g) and potassium hydroxide (8.96 g) was dissolved in 34.54 g of distilled water with stirring while cooling to below 30 degrees C. Using an addition funnel, acrylic acid (19.38 g) was charged slowly and the temperature was maintained below 40 degrees C. After adding and dissolving potassium-3-sulfopropylacrylate (15.62 g), polyacrylamide N-300 LMW (2.0 g) was then added and dispersed into the above solution with vigorous stirring. The polyacrylamide dissolved slowly over a period of a few hours with a corresponding increase in the viscosity of the solution. Glycerin (17.0 g); a 3% solution of N,N'methylenebis acrylamide in propylene glycol (1.2 g); and Darocur 1173 (0.8 g) were then added sequentially, with stirring, resulting in a moderately viscous, homogeneous solution.

In the description given above in Example 4 for the formation of an adhesive hydrogel, as in Example 1, the distilled water serves as a solvent and potassium chloride is added as an electrolyte to provide electrical conductivity. Potassium hydroxide, polyacrylamide polymer, glycerin, MBA, and Darocur 1173 serve the same functions as indicated in Example 1.

The finished composition was coated onto a polycarbonate film having a thickness of 2.5 mil, using a 30 mil wet-film applicator. The coating was cured as in Example 1. A hydrogel adhesive was thus formed of a copolymer of SPAK and acrylic acid. Peel adhesion, tack adhesion, creep compliance, and repositionability of the adhesive were then measured as in Example 1. The peel adhesion characteristics of a set of hydrogel adhesive copolymers prepared from acrylic acid as the second water soluble monomer and SPAK as the first are shown as Examples 1–7 in Table 1 and in FIG. 1. The peel adhesion values exhibited by both of the homopolymers (40 g for the SPAK homopolymer and 30 g for the AA homopolymer) are low but adequate, for example, on applications on highly sensitive skin. The peel adhesion values of the copolymers are higher, however, than each of the homopolymers and increase to a peak level at a SPAK concentration of approximately 30–70 weight percent of the total monomer. The peak peel adhesion values for the copolymer are approximately 460 g, over ten times that of either of the homopolymers. The magnitude of the increased peel adhesion of copolymers having 25–75 weight % SPAK of total monomer (75–25 weight % AA of total monomer, respectively) over the homopolymers is unexpected. (See FIG. 1.)

Figure 1:
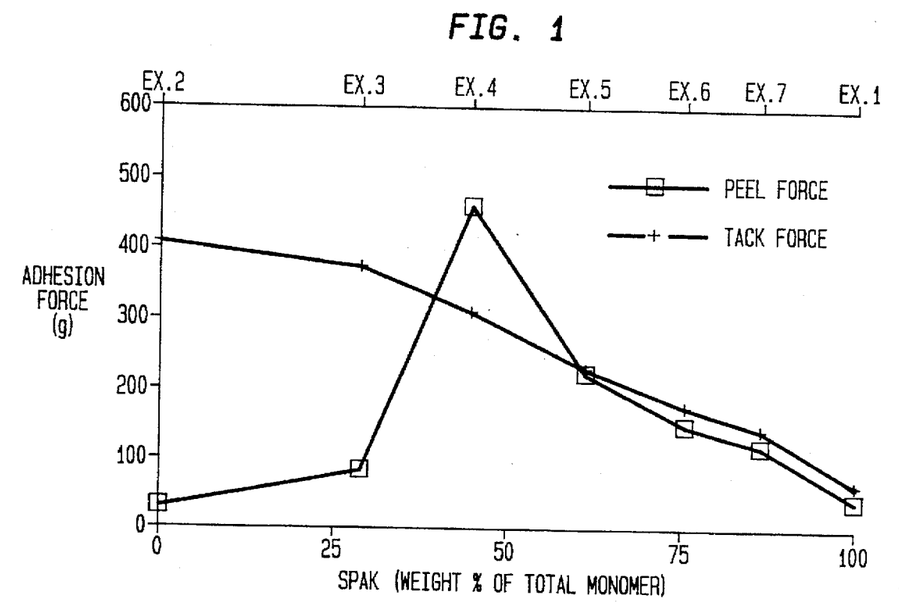
FIG. 1 is a graph depicting properties of a set of hydrogel adhesives prepared from exemplary formula (I) and formula (II) monomers.

That the increase and peak in peel strength is unexpected is illustrated partly by the more linear variation in the tack adhesion of the same compositions as shown in FIG. 1. Given this more linearized plot, linear variance of peel adhesion would also be expected. The variation in tack adhesion is almost linear and decreases as the concentration of SPAK in the copolymer increases.

The SPAK/AA copolymer in hydrogel adhesive form is a particularly useful composition because it provides a continuum of hydrogel adhesives which can be used in a broad spectrum of applications. The applications can have requirements varying from a relatively weak, skin-friendly, repositionable adhesive (where a composition having a concentration close to either 100% SPAK or 0% SPAK would be appropriate) to an aggressive, very strong adhesive, desirable in such dynamic or long-term applications as ECG or Holter monitoring (where a 30–70% SPAK composition would be appropriate). Any intermediate adhesive characteristics which may be desired can also be produced. One should also appreciate that by varying the concentrations of the various components in the compositions, the peel adhesion peak can be shifted anywhere in the range of 10–90% by weight SPAK of total monomer.

Figure 2:
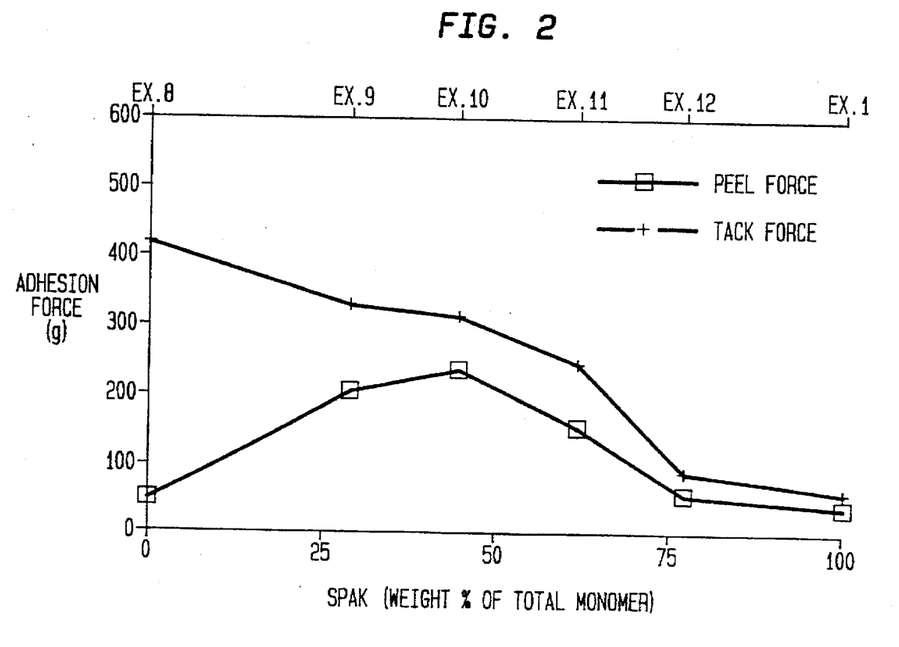
FIG. 2 is a graph depicting properties of another set of hydrogel adhesives prepared from further exemplary formula (I) and formula (II) monomers.

Other monomers can also be used as the second water soluble monomer. Hydrogel adhesive copolymers prepared from acrylamide as the second monomer (AAM) and SPAK as the first possess synergistic adhesion properties analogous to those observed for SPAK/AA copolymers. (See the compositions and their corresponding adhesion data in Examples 8–12 in Table 2 and FIG. 2.) Similar to the other homopolymers described above, the peel adhesion exhibited by the AAM homopolymer (0% SPAK) is very low. Nevertheless, the peel adhesion of the copolymer increases and peaks at a SPAK concentration of approximately 20–70 weight percent of total monomer.

Although acrylic acid and acrylamide are the only specific examples of the second monomer given, alkylated acrylamides are reasonable extensions of acrylamide because they have similar polarity and size. Vinyl pyrrolidone is also similar in size and polarity to dialkylated acrylamides. Sulfonic acid and phosphoric acid groups are reasonable extensions of the carboxylic acid group because they are also similar in size and polarity especially when neutralized to their anionic form. All of these monomers are within the scope of Formula II.

Turning to the second of the two formula I monomers which specifically illustrate the advantageous properties of the acrylate ester hydrogels of the present invention, CEA, it should be noted that the CEA which was used in the examples described herein is not a pure material. The CEA (or 2-carboxyethylacrylate) was obtained from Radcure Specialties Inc. of Louisville, Ky. It consists of a mixture of approximately 20% AA, 40% CEA, and 40% of a mixture of polyester trimers and tetramers having the following structure:

where n=0 for CEA, n=1 for trimer, and n=2 for tetramer. Therefore, all of the hydrogel polymers and copolymers of CEA contain substantial quantities of polyester trimer and tetramer units and AA units as well as CEA. All numbers in the examples are corrected to account for the presence of these other substances.

Figure 3:
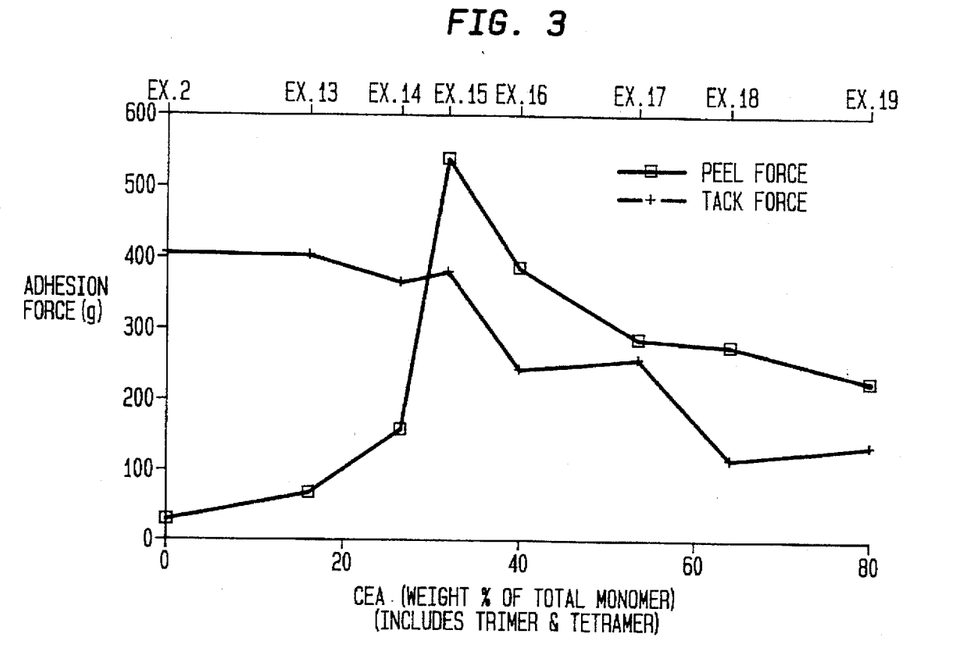
FIG. 3 is a graph depicting properties of another set of hydrogel adhesives prepared from further exemplary formula (I) and formula (II) monomers.
Figure 4:
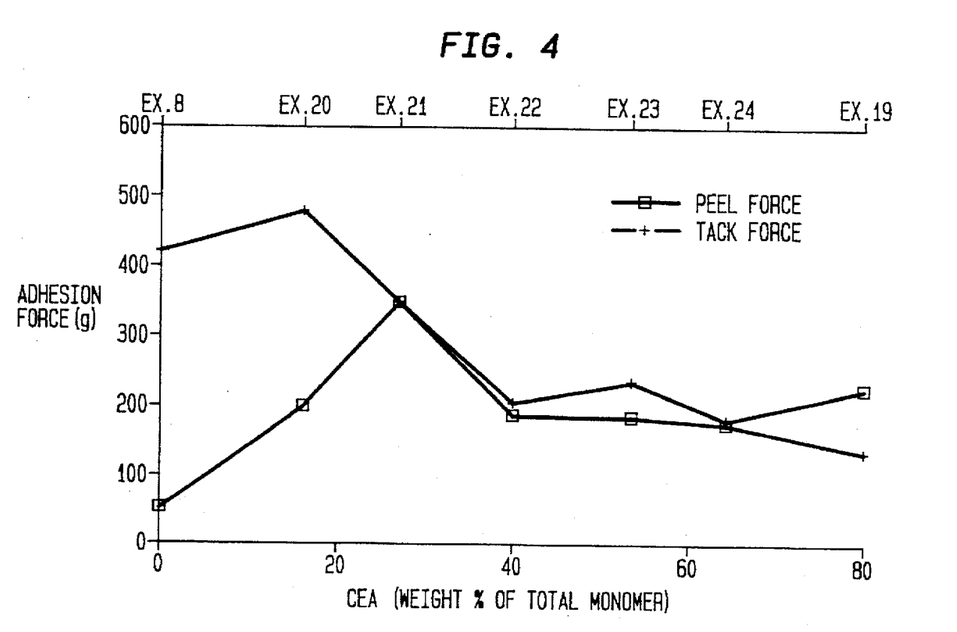
FIG. 4 is a graph depicting properties of another set of hydrogel adhesives prepared from further exemplary formula (I) and formula (II) monomers.

CEA copolymers with AA or AAM (Examples 13–24, Tables 3 and 4, and FIGS. 3 and 4) exhibit adhesive behavior similar to that of the SPAK examples discussed above. The CEA as purchased (with 20% AA), which exhibits a 230 g peel adhesion, also possesses desirable repositionability properties. Copolymers of CEA with AA or AAM exhibit a surprising peel adhesion behavior within a useful range of peel adhesion values. In particular, peel adhesion values are surprisingly high when CEA is 20–75 weight % of the total monomer. The surprising peel adhesion behavior of CEA copolymers demonstrates that esters of longer chain length than SPAK or pure CEA also confer advantageous adhesion properties on the hydrogels of the present invention. Because the CEA used in the examples contains 40% of a mixture of trimer and tetramer which have 7 and 12 chain atoms, respectively, extrapolation to pure alkyl groups and ether groups is reasonable because these groups have similar hydrophobicity and polarity to the ester groupings present in CEA trimer and tetramer. Therefore, these groups are included in the general formula I for the first water soluble monomer.

Figure 5:
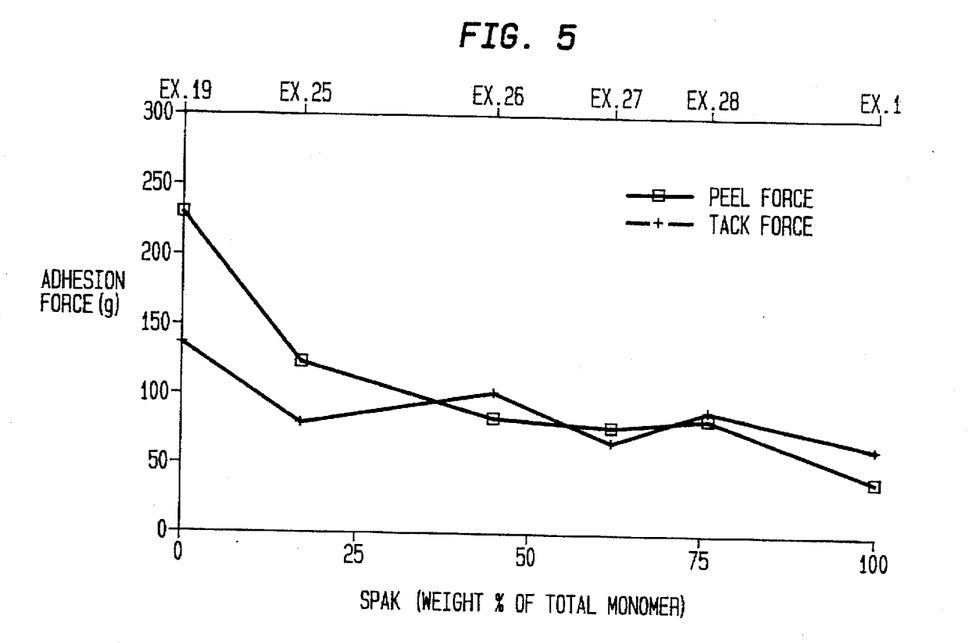
FIG. 5 is a graph depicting properties of a set of hydrogel adhesives prepared from two exemplary formula (I) monomers.

Hydrogel copolymer adhesives prepared from various ratios of SPAK and CEA together (i.e., two Formula I monomers) do not exhibit the surprising peel adhesion characteristics. Instead, a nearly linear relationship between the peel adhesion and the tack adhesion of the two homopolymers is observed (Examples 25–28, Table 5, and FIG. 5). Because both SPAK and CEA are long-chain acrylate ester monomers, it is evident that only copolymers which combine long-chain acrylate ester monomers with monomers of small molecular size, such as AA or AAM, will exhibit the synergistic peel adhesion properties.

Hydrogel adhesive polymers were also prepared from methacrylate ester monomers as the Formula I monomers (Table 6) such as 2-sulfoethylmethacrylate (SEMA, Examples 29, 33, and 34) and potassium-3-sulfopropyl methacrylate (SPMAK, Examples 30 and 32). Methacrylate ester monomers are much less reactive to UV free radical initiation than are acrylate ester monomers such as SPAK and CEA; therefore, the formation of polymers comprising these compounds was initiated using thermal free radical initiator procedures. The thermal initiator used was V-50 (2,2'-azobis (2-amidinopropane) dihydrochloride) (available from Wako Chemicals, U.S.A. Inc. of Richmond, Va.). The methacrylate monomers formed hydrogel adhesive polymers which were tacky and adhesive to the touch and may be as useful as the corresponding acrylate polymer hydrogels.

A cationic-terminated, methacrylate ester-based hydrogel adhesive was prepared by thermal initiation of the methacryloxyethyl trimethylammonium chloride monomer (MAETAC, Examples 31 and 34) having the following structure:

The resulting hydrogel polymer was also tacky and adhesive to the touch and appears to be as useful as all of the preceding examples.

Figure 6:
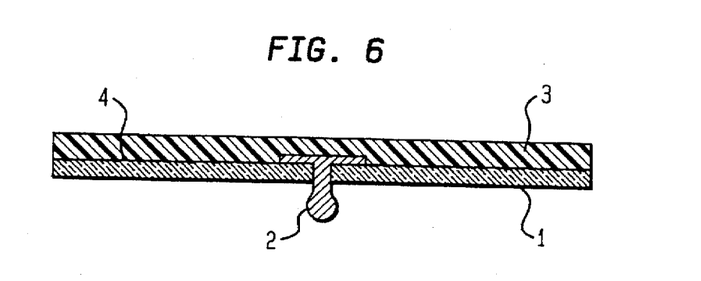
FIG. 6 is a cross-sectional view illustrating an exemplary biomedical electrode including a hydrogel adhesive of the present invention.

A particularly useful application of the hydrogel adhesives of the present invention is with biomedical electrodes. The adhesives are useful in a wide variety of electrodes assuming varying construction. FIG. 6 is an exemplary embodiment of one of these electrodes.

In FIG. 6, a support member 1, which is circular in shape in this exemplary embodiment, is made of a plastic substance. Electrode 2 is incorporated in support member 1 so as to protrude from both sides of support member 1. An electrically conductive hydrogel adhesive 3, having a composition according to the present invention, is superposed on surface 4 of support member 1 and is adapted to be adhered to the skin of a patient. Hydrogel adhesive 3 should be applied to surface 4 in a thickness sufficient to cover the portion of electrode 2 protruding from surface 4 of support member 1.

In use, electrode 2 is connected to a measuring instrument (not shown) and the electrically conductive hydrogel adhesive 3 is pressed against the patient with sufficient pressure to adhere the biomedical electrode to the patient.

Figure 7:
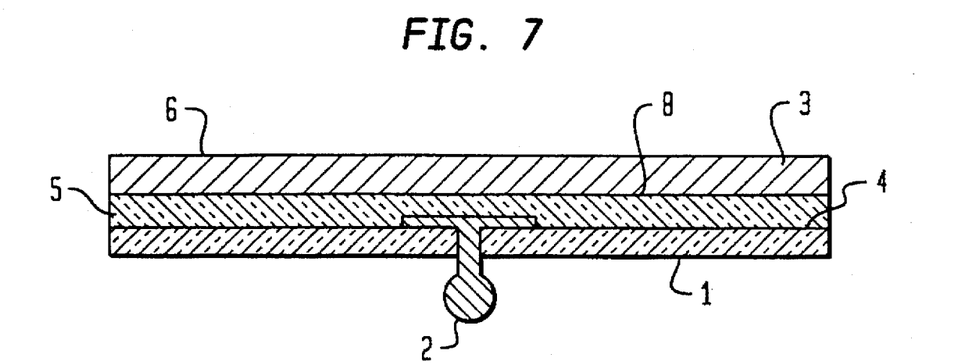
FIG. 7 is a cross-sectional view illustrating an alternative exemplary biomedical electrode according to the present invention.

The hydrogel adhesives of the present invention may also be used in conjunction with gas permeable substrates in many applications. FIG. 7 shows a biomedical electrode exemplifying this embodiment of the invention. Between hydrogel adhesive 3 and surface 4 of support member 1 is gas permeable substrate 5. Gas permeable substrate 5 may be attached to surface 4 by a conventional pressure sensitive adhesive or other means known in the art. Alternatively, support member 1 may itself be gas permeable, thus eliminating the need to use an extra layer between support member 1 and hydrogel adhesive 3. The adhesive properties of hydrogel adhesive 3 attach it to gas permeable substrate 5.

A variety of substrates are available that have a wide range of physical properties. The substrates vary in flexibility, stiffness, thickness, transparency, and gas permeability, among other properties. These properties may be evaluated for particular applications of the hydrogel adhesive on a substrate so that an appropriate substrate may be selected. For example, a substrate that is flexible and transparent is best suited for use in medical tape applications, while a stiff substrate, without regard for transparency is suitable for use in medical electrode applications.

Suitable materials available for use as a gas permeable substrate are Tyvek, E. I. DuPont de Nemours Corp., Wilmington Del.; Versapor, Gelman Sciences, Ann Arbor, Mich.; Typar, Reemay, Kennett Square, Pa.; Flexel, Flexel Inc., Atlanta, Ga.; Kleer Kast, Technical Plastic Extruders, Inc., Newark, N.J.; Semex, Semex Medical Coated Products, Frazer, Pa.; Deerfield, Deerfield Urethane, A Miles Inc. Co., South Deerfield, Mass.; and Teslin, PPG Industries Inc., Pittsburgh, Pa. Preferred materials are Tyvek 1073, Teslin 10, Deerfield 2, and Flexel.

The embodiment illustrated in FIG. 7 is only one of a large number of applications for the hydrogel adhesive on a gas permeable substrate. Other applications include use in medical devices such as wound dressings, transdermal drug delivery systems, iontophoretic drug delivery systems, medical tape, ostomy devices, monitoring ECG electrodes, serial ECG electrodes, diaphoretic and stress electrodes, Holter electrodes, electrosurgical grounding pads, surgical drapes, transdermal electrical nerve stimulation electrodes, suture strips, and bandages.

Two significant advantages may be achieved using the hydrogel adhesive on a gas permeable substrate. First, a medical device such as the electrode shown in FIG. 7 can control the moisture level at the adhesive/skin interface. Surface 6 of hydrogel adhesive 3 in FIG. 7 is attached to a patient's skin. The adhesive skin interface is at surface 6. An adhesive on skin typically absorbs moisture continuously from the skin. This absorption of moisture gradually weakens the bonding strength of the adhesive to the skin if the adhesive is occlusive. By using gas permeable substrate 5 behind hydrogel adhesive 3, moisture that is absorbed from the skin at surface 6 can pass from hydrogel adhesive 3 to gas permeable substrate 5. In addition, the moisture may evaporate out the side of gas permeable substrate 5 opposite hydrogel adhesive 3 if no support member 1 is used or if support member 1 itself is gas permeable. Evaporation of the moisture maintains a balanced moisture level at the adhesive/skin interface, which is essential for long-term adhesion of a device to the skin.

The second advantage of using hydrogel adhesives on gas permeable substrates is that moisture does not accumulate at the adhesive/skin interface at surface 6. A high moisture level accumulated at the adhesive/skin interface may cause skin maceration, irritation, discomfort, and possibly bacterial proliferation. By using hydrogel adhesive 3 on gas permeable substrate 5, moisture can continually migrate away from the adhesive/skin interface at surface 6, through hydrogel adhesive 3 and gas permeable substrate 5, and out to the atmosphere.

Because the hydrogel adhesives of the present invention are hydrophilic, and because water is used as the solvent in these adhesives, water transmission inside the hydrogel adhesive is basically unrestricted. Water absorbed from skin may move easily from the skin/adhesive interface at surface 6 to the adhesive/substrate interface at surface 8. The water then evaporates through the gas permeable substrate 5 until equilibrium is reached. The equilibrium level and the time required to reach it depends on several factors, such as the type of skin, the environment (i.e., temperature and humidity), the dry-out resistance of the hydrogel, and the permeability of the substrate (its water vapor transmission rate).

Tables 7 and 8 show results obtained from tests performed on hydrogel adhesives on a variety of substrates. The substrates are listed in the left hand column, along with their respective water vapor transmission rates (WTVR) in the next column. Each of the substrates in Table 7 was coated with a hydrogel adhesive according to the present invention, having the following composition (in weight percents): distilled water (20.70); potassium chloride (0.50); triethanolamine (17.46); acrylic acid (16.87); SPAK (18.13); hydroxyethyl cellulose (0.40); glycerin (23.94); 3% methylenebis-acrylamide (1.20); and Darocur 1173 (0.80). Each of the substrates in Table 8 was coated with a hydrogel adhesive according to the present invention, having the following composition (in weight percents): distilled water (21.16); potassium chloride (1.00); potassium hydroxide (6.01); acrylic acid (13.25); SPAK (14.25); hydroxyethyl cellulose (0.50); glycerin (42.27); 3% methylenebis-acrylamide (1.40); and Darocur 1173 (0.16).

The average peel force (A.P.F.) of each of the adhesive-substrate samples was then measured after being adhered to skin for two minutes and again after being adhered to skin for 24 hours. The weight retention of each sample was also measured after 24 hours (weight of adhesive-substrate sample after 24 hours on the skin divided by the original weight of the sample).

Table 9 shows the results of similar tests performed on two samples, with peel force measured at 24 hour intervals. The two samples have the same substrate, but different hydrogels on them. The hydrogels differ in their dry-out resistance. The first four substrates listed in Table 9 were coated with a hydrogel adhesive according to the present invention, having the following composition (in weight percents): distilled water (18.44); potassium chloride (0.50); triethanolamine (16.28); acrylic acid (15.57); SPAK (16.93); hydroxyethyl cellulose (0.40); glycerin (29.68); 3% methylenebis-acrylamide (1.40); and Darocur 1173 (0.80). The last four substrates listed were coated with hydrogel adhesive according to the present invention, having the following composition (in weight percents): distilled water (20.70); potassium chloride (0.50); triethanolamine (17.46); acrylic acid (16.87); SPAK (18.13); hydroxyethyl cellulose (0.40); glycerin (23.94); 3% methylenebis-acrylamide (1.20); and Darocur 1173 (0.80).

The results of Tables 7–9 show that the peel adhesion of the samples on skin after two minutes is quite close for the same hydrogels. After 24 hours, significant differences may be seen. The results show that if the hydrogel gains more than 5% weight after 24 hours on the skin, the peel force decreases considerably. If the weight of the sample remains within 3% (which is accomplished by matching the hydrogel and the substrate to achieve equilibrium), the peel adhesion remains relatively constant. If the hydrogel loses more than 5% of its original weight, using a high WVTR substrate, its peel strength on skin is enhanced.

The results shown in Tables 7, 8, and 9 suggest that coating different hydrogels on various WVTR substrates provides a family of skin adhesives with different permeability that can meet a variety of applications.

The main components of the adhesive hydrogels of this invention are hydrophilic polymers, which provide adhesive and cohesive properties to the system. These polymers include poly(potassium-3-sulfopropyl acrylate), poly(2-carboxyethyl acrylate), polyacrylic acid, and polyacrylamide. Water is used in the adhesive as a solvent to give the adhesives skin-friendliness and conductivity. A humectant may be used as a co-solvent to provide slow dry-out or non-dry-out characteristics. Electrolytes such as sodium chloride for electrical conductivity are optional components depending on the application. The properties of adhesiveness, dry-out resistance, and conductivity of the hydrogel adhesives of the present invention may be engineered, depending on the requirements of particular applications, by optimizing the ratio of long side chain monomer (Formula I) to short side chain monomer (Formula II). In addition, the ratio of polymer to solvent and the ratio of water to humectant, as well as the concentration of salts, may be varied to adjust the properties. Because high water absorptivity is one of the characteristics of hydrogels, combining this feature with a high water vapor transmission rate substrate provides another advantage to the system for certain applications such as wound dressing and ostomy device where evaporation of moisture from the adhesive/skin interface is important.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

TABLE 1

| Composition (% by weight) | Example Number | | | | | | |
| --- | --- | --- | --- | --- | --- | --- | --- |
| | 1 | 2 | 3 | 4 | 5 | 6 | 7 |
| Distilled Water | 40.05 | 29.77 | 32.86 | 34.54 | 36.36 | 37.95 | 39.05 |
| Potassim Chloride | 0.5 | 0.5 | 0.5 | 0.5 | 0.5 | 0.5 | 0.5 |
| Potassium Hydroxide | — | 16.12 | 11.49 | 8.96 | 6.24 | 3.85 | 2.19 |
| Acrylic Acid | — | 35 | 24.95 | 19.38 | 13.4 | 8.29 | 4.7 |
| SPAK | 35 | — | 10.05 | 15.62 | 21.6 | 26.71 | 30.03 |
| PAAm N-300 LMW | 2 | 2 | 2 | 2 | 2 | 2 | 2 |
| Glycerin | 20 | 14.61 | 16.15 | 17 | 17.9 | 18.7 | 19.26 |
| 3% MBA/PG | 1.2 | 1.2 | 1.2 | 1.2 | 1.2 | 1.2 | 1.2 |
| Darocur-1173 | 0.8 | 0.8 | 0.8 | 0.8 | 0.8 | 0.8 | 0.8 |
| Ave. Peel Force (g) | 40 | 30 | 85 | 460 | 225 | 150 | 120 |
| Tack Force (g) | 63 | 408 | 375 | 310 | 233 | 175 | 144 |

TABLE 2

| Composition (% by weight) | Example Number | | | | |
| --- | --- | --- | --- | --- | --- |
| | 8 | 9 | 10 | 11 | 12 |
| Distilled Water | 40.5 | 40.5 | 40.5 | 40.5 | 40.5 |
| Potassium Chloride | 0.5 | 0.5 | 0.5 | 0.5 | 0.5 |
| Acrylamide | 35 | 24.85 | 19.26 | 13.29 | 8.2 |
| SPAK | — | 10.15 | 15.74 | 21.72 | 26.8 |
| PAAm N-300 LMW | 2 | 2 | 2 | 2 | 2 |
| Glycerin | 20 | 20 | 20 | 20 | 20 |
| 3% MBA/PG | 1.2 | 1.2 | 1.2 | 1.2 | 1.2 |
| Darocur-1173 | 0.8 | 0.8 | 0.8 | 0.8 | 0.8 |
| Ale. Peel Force (g) | 50 | 210 | 240 | 160 | 60 |
| Tack Force (g) | 420 | 330 | 315 | 250 | 93 |

TABLE 3

| Composition (% by weight) | Example Number | | | | | | |
|---|---|---|---|---|---|---|---|
| | 13 | 14 | 15 | 16 | 17 | 18 | 19 |
| Distilled Water | 31.06 | 31.39 | 31.72 | 32.21 | 33.27 | 33.95 | 35.11 |
| Potassium Chloride | 0.5 | 0.5 | 0.5 | 0.5 | 0.5 | 0.5 | 0.5 |
| Potassium Hydroxide | 14.44 | 13.36 | 12.82 | 12.03 | 10.69 | 9.62 | 7.93 |
| AA (including the 20% AA in the CEA as purchased) | 29.4 | 25.66 | 23.8 | 21 | 16.34 | 12.6 | 7 20% |
| CEA (including the tri- and tetra-mers) | 5.6 | 9.34 | 11.2 | 14 | 18.66 | 22.4 | 28 |
| PAAm N-300 LMW | 2 | 2 | 2 | 2 | 2 | 2 | 2 |
| Glycerin | 15 | 15.75 | 15.96 | 16.26 | 16.54 | 16.93 | 17.46 |
| 3% MBA/PG | 1.2 | 1.2 | 1.2 | 1.2 | 1.2 | 1.2 | 1.2 |
| Darocur-1173 | 0.8 | 0.8 | 0.8 | 0.8 | 0.8 | 0.8 | 0.8 |
| Ave. Peel Force (g) | 70 | 160 | 540 | 390 | 290 | 280 | 230 |
| Tack Force (g) | 406 | 366 | 384 | 244 | 261 | 117 | 138 |

TABLE 4

| Composition | Example Number | | | | |
|---|---|---|---|---|---|
| (% by weight) | 20 | 21 | 22 | 23 | 24 |
| Distilled water | 39.21 | 38.49 | 37.6 | 36.72 | 36 |
| Potassium Chloride | 0.5 | 0.5 | 0.5 | 0.5 | 0.5 |
| Potassium Hydroxide | 1.62 | 2.7 | 4.04 | 5.37 | 6.44 |
| Acrylamide | 27.92 | 23.22 | 17.37 | 11.56 | 6.92 |
| CEA (including tri- and tetra-mers | 5.66 | 9.42 | 14.1 | 18.75 | 22.46 |
| AA (20% of CEA as purchased) | 1.42 | 2.36 | 3.53 | 4.69 | 5.62 |
| PAAm N-300 LMW | 2 | 2 | 2 | 2 | 2 |
| Glycerin | 19.67 | 19.31 | 18.86 | 18.42 | 18.06 |
| 3% MBA/PG | 1.2 | 1.2 | 1.2 | 1.2 | 1.2 |
| Darocur-1173 | 0.8 | 0.8 | 0.8 | 0.8 | 0.8 |
| Ave. Peel Force (g) | 200 | 350 | 190 | 190 | 180 |
| Tack Force (g) | 480 | 351 | 206 | 240 | 183 |

TABLE 5

| Composition (% by weight) | Example Number | | | |
|---|---|---|---|---|
| | 25 | 26 | 27 | 28 |
| Distilled Water | 36 | 39.34 | 38.38 | 39.02 |
| Potassium Chloride | 0.5 | 0.5 | 0.5 | 0.5 |
| Potassium Hydroxide | 6.6 | 4.44 | 3.04 | 1.9 |
| CFA (including tri-& tetra-mers) | 23.30 | 15.50 | 10.72 | 6.63 |
| AA (20% of CEA as purchased) | 5.83 | 3.88 | 2.68 | 1.66 |
| SPAK | 5.87 | 15.62 | 21.6 | 26.71 |
| PAAm N-300 LMW | 2 | 2 | 2 | 2 |
| Glycerin | 17.9 | 18.72 | 19.08 | 19.58 |
| 3% MBA/PG | 1.2 | 1.2 | 1.2 | 1.2 |
| Darocur-1173 | 0.8 | 0.8 | 0.8 | 0.8 |
| Ave. Peel Force (g) | 125 | 85 | 80 | 85 |
| Tack Force (g) | 80 | 104 | 68 | 91 |

TABLE 6

| Composition (% by weight) | Example Number | | | | | |
|---|---|---|---|---|---|---|
| | 29 | 30 | 31 | 32 | 33 | 34 |
| Distilled Water | 38.7 | 42.7 | 47.67 | 39.87 | 37.51 | 39.9 |
| Potassium Chloride | 0.5 | 0.5 | 0.5 | 0.5 | 0.5 | 0.5 |
| Potassium Hydroxide | 5.95 | — | — | 3.59 | 6.84 | 3.25 |
| Acrylic Acid | — | — | — | 7.92 | — | — |
| SEMA | 35 | — | — | — | 20.09 | 14.34 |
| CEA (including tri- & tetra-mers | — | — | — | — | 11.93 | — |
| AA (20% of CEA as purchased) | — | — | — | — | 2.98 | — |
| SPMAK | — | 35 | — | 27.08 | — | — |
| MAETAC | — | — | 35 | — | — | 20.66 |
| Glycerin | 18.45 | 20.4 | 15.43 | 19.04 | 17.95 | 19.15 |
| 3% MBA/PG | 1.2 | 1.2 | 1.2 | 1.8 | 1.8 | 1.8 |
| V-50 | 0.2 | 0.2 | 0.2 | 0.2 | 0.4 | 0.4 |

TABLE 7

| Substrate | WVTR g/sq meter/24 hr | A.P.F. on Skin* 2 min., g | A.P.F. on Skin 24 hours, g | Weight Retention 24 hrs. on skin, % |
| --- | --- | --- | --- | --- |
| Tyvek 1059B | 650 | 180 | 410 | 95 |
| Versapor 200R | 850 | 150 | 440 | 93 |
| Versapor 1200H | 870 | 190 | 450 | 94 |
| Typar | 90 | 120 | 100 | 107 |
| Flexel | 580 | 150 | 370 | 95 |
| Kleer Kast | 120 | 155 | 65 | 110 |
| Semox 01 | 740 | 110 | 230 | 95 |
| Semex 02 | 400 | 190 | 250 | 97 |
| Deerfield 1 | 180 | 210 | 220 | 100 |
| Deerfield 2 | 100 | 180 | 120 | 105 |
| Deerfield 6 | 70 | 190 | 80 | 108 |
| Foil Pouch | 1 | 130 | 55 | 110 |

TABLE 8

| Substrate | WVTR g/sq meter/24 hr | Substrate Thickness mil | A.P.F. on Skin* 2 min., g | A.P.F. on Skin 24 hours, g | Weight Retention 24 hrs. on skin, % |
| --- | --- | --- | --- | --- | --- |
| Tyvek 1059B | 650 | 6 | 230 | 440 | 93 |
| Tyvek 1073B | 780 | 7 | 240 | 410 | 94 |
| Tyvek 1085D | 610 | 10 | 250 | 320 | 94 |
| Teslin 7 | 810 | 7 | 210 | 380 | 89 |
| Teslin 8 | 780 | 8 | 200 | 280 | 89 |
| Teslin 10 | 750 | 10 | 200 | 350 | 91 |
| Teslin 12 | 700 | 12 | 150 | 280 | 91 |
| Teslin 14 | 560 | 14 | 125 | 230 | 92 |
| Teslin 18 | 490 | 18 | 195 | 280 | 94 |
| Polyethylene | 6 | 6 | 200 | 40 | 118 |

TABLE 9

| Substrate | WVTR g/sq meter/24 hr | Duration on skin hours | A.P.F. on Skin g | Weight Retention on the time, % |
| --- | --- | --- | --- | --- |
| Tyvek 1059B | 650 | 0 | 170 | 100 |
| Tyvek 1059B | 650 | 24 | 150 | 99 |
| Tyvek 1059B | 650 | 48 | 160 | 98 |
| Tyvek 1059B | 650 | 72 | 140 | 99 |
| Tyvek 1059B | 650 | 0 | 150 | 100 |
| Tyvek 1059B | 650 | 24 | 280 | 95 |
| Tyvek 1059B | 650 | 48 | 290 | 95 |
| Tyvek 1059B | 650 | 72 | 170 | 98 |

What is claimed:

1. A biomedical device comprising a hydrogel adhesive containing a copolymer of a first water soluble monomer having the structure (I)

$$CH_2=C(R_1)-C(=O)-O-R_2-X \quad (I)$$

where, $R_1$ is selected from the group consisting of H and $CH_3$;

$R_2$ is selected from the group consisting of a straight or branched chain alkyl radical of 2–12 carbon atoms, a straight or branched chain aliphatic ester of 5–12 carbon and oxygen atoms, and a straight or branched chain ether radical of 3–12 carbon and oxygen atoms;

X is an ionic group selected from the group consisting of $SO_3^-$, $COO^-$ and $$\begin{array}{c} R_3 \\ | \\ {}_+N-R_4 \\ | \\ R_5 \end{array}$$

where $R_3$, $R_4$, and $R_5$ are independently selected from the group consisting of H and alkyl groups of 1–4 carbon atoms;

copolymerized and cross-linked in the presence of water, a multi-functional cross-linking agent, and a humectant with a second water soluble monomer having the structure (II)

$$CH_2=CH-Y \quad (II)$$

where Y is selected from the group consisting of

—COOH,

—SO$_3$H, and —PO$_3$H where R$_6$, R$_7$ are independently selected from the group consisting of H and alkyl groups of 1–3 carbon atoms;

wherein said first water soluble monomer is selected from the group consisting of potassium-3-sulfopropyl acrylate, potassium-3-sulfopropyl methacrylate, 2-carboxyethylacrylate, 2-sulfoethylmethacrylate, and methacryloxyethyl trimethylammonium chloride; and wherein said second water soluble monomer is selected from the group consisting of acrylic acid, acrylamide, alkylated acrylamides, vinyl pyrrolidone, vinyl sulfonic acid, and vinyl phosphonic acid.

2. A biomedical device as claimed in claim 1 further comprising a gas permeable substrate adjacent to said hydrogel adhesive.

3. A biomedical device as claimed in claim 1 wherein said first water soluble monomer comprises 10–90 weight % of total monomer weight.

4. A biomedical device as claimed in claim 1 wherein said first water soluble monomer is selected from the group consisting of potassium-3-sulfopropyl acrylate and potassium-3-sulfopropyl methacrylate, said second water soluble monomer is acrylic acid, and said first water soluble monomer comprises 10–90 weight % of total monomer weight.

5. A biomedical device as claimed in claim 1 wherein said first water soluble monomer is selected from the group consisting of potassium-3-sulfopropyl acrylate and potassium-3-sulfopropyl methacrylate, and said second water soluble monomer is acrylamide, and said first water soluble monomer comprises 20–70 weight % of total monomer weight.

6. A biomedical device as claimed in claim 1 wherein said first water soluble monomer is 2-carboxyethylacrylate, said second water soluble monomer is acrylic acid, and said first water soluble monomer comprises 20–75 weight % of total monomer weight.

7. A biomedical device as claimed in claim 1 wherein said first water soluble monomer is 2-carboxyethylacrylate, said second water soluble monomer is acrylamide, and said first water soluble monomer comprises 10–50 weight % of total monomer weight.

8. A biomedical device comprising:

(a) a hydrogel adhesive containing a copolymer of a first water soluble monomer having the structure (I)

(I)

where,

R$_1$ is selected from the group consisting of H and CH$_3$;

R$_2$ is selected from the group consisting of a straight or branched chain alkyl radical of 2–12 carbon atoms, a straight or branched chain aliphatic ester of 5–12 carbon and oxygen atoms, and a straight or branched chain ether radical of 3–12 carbon and oxygen atoms;

X is an ionic group selected from the group consisting of SO$_3^-$, COO$^-$ and where R$_3$, R$_4$, and R$_5$ are independently selected from the group consisting of H and alkyl groups of 1–4 carbon atoms;

copolymerized and cross-linked in the presence of water, a multi-functional cross-linking agent, and a humectant with a second water soluble monomer having the structure (II)

(II)

where Y is selected from the group consisting of
—COOH,

—SO$_3$H, and —PO$_3$H where R$_6$, R$_7$ are independently selected from the group consisting of H and alkyl groups of 1–3 carbon atoms; and (b) a gas permeable substrate adjacent to said hydrogel adhesive;

wherein said first water soluble monomer is selected from the group consisting of potassium-3-sulfopropyl acrylate, potassium-3-sulfopropyl methacrylate, 2-carboxyethylacrylate, 2-sulfoethylmethacrylate, and methacryloxyethyl trimethylammonium chloride;

and wherein said second water soluble monomer is selected from the group consisting of acrylic acid, acrylamide, alkylated acrylamides, vinyl pyrrolidone, vinyl sulfonic acid, and vinyl phosphonic acid;

said first water soluble monomer comprising 10–90 weight % of total monomer weight.

* * * * *